United States Patent [19]

Blizzard

[11] Patent Number: 5,077,308

[45] Date of Patent: Dec. 31, 1991

[54] AVERMECTIN KETAL DERIVATIVES USEFUL AS ANTIPARASITIC

[75] Inventor: Timothy A. Blizzard, Rahway, N.J.

[73] Assignee: Merck & Co., Inc., Rahway, N.J.

[21] Appl. No.: 556,044

[22] Filed: Jul. 23, 1990

Related U.S. Application Data

[63] Continuation of Ser. No. 311,268, Feb. 16, 1989, abandoned.

[51] Int. Cl.$^5$ .................. A61K 31/365; C07D 493/22
[52] U.S. Cl. .................. 514/450; 549/264; 549/265
[58] Field of Search .............. 549/264, 265; 514/450

[56] References Cited

U.S. PATENT DOCUMENTS

| Re. 32,006 | 10/1975 | Chabala et al. | 549/264 |
| Re. 32,032 | 11/1985 | Chabala et al. | 549/264 |
| 3,950,360 | 4/1976 | Aoki et al. | 549/264 |
| 4,200,581 | 4/1980 | Fisher et al. | 549/264 |
| 4,310,519 | 1/1982 | Albers-Schonberg et al. | 536/7.1 |
| 4,547,520 | 10/1985 | Ide et al. | 549/264 |
| 4,696,945 | 9/1987 | Frei et al. | 549/264 |

FOREIGN PATENT DOCUMENTS

| 170006 | 2/1986 | European Pat. Off. | |
| 0284563 | 3/1988 | European Pat. Off. | 549/264 |
| 2166436 | 5/1986 | United Kingdom | 549/264 |

OTHER PUBLICATIONS

H. Mrozik et al., *J. Org. Chem.*, "Avermectin Aglycons," 47(3), pp. 489–492 (1982).
G. Carter et al., *J. Antiobiotics*, "LL-F28249 Antibiotic Complex," 41(4), pp. 519–529 (1988).
G. Albers-Schönberg et al., *J. Am. Chem. Soc.*, "Avermectins Structure Determination," 103(14), pp. 4216–4221 (1981).
J. Chabala et al., *J. Med. Chem.*, "Avermectin, a New Broad-Spectrum Antiparasitic Agent," 23(10), 1134–1136 (1980).

*Primary Examiner*—Richard L. Raymond
*Assistant Examiner*—Mark W. Russell
*Attorney, Agent, or Firm*—David L. Rose; Joseph F. DiPrima

[57] ABSTRACT

There are disclosed avermectin aglycone derivatives which incorporate a ketal at position 13. The synthetic ketal analogs are derived from the corresponding ketones which in turn are prepared by chemical modification of naturally occurring avermectins. The compounds are active antiparasitic agents and compositions for that use are disclosed.

16 Claims, No Drawings

AVERMECTIN KETAL DERIVATIVES USEFUL AS ANTIPARASITIC

This is a continuation of application Ser. No. 311,268, filed Feb. 16, 1989 now abandoned.

BACKGROUND OF THE INVENTION

The avermectins (previously referred to as C-076 compounds) are a series of compounds produced by fermentation of avermectin producing strains of *Streptomyces avermitilis* and derivatives thereof. The morphological characteristics of the culture are completely described in U.S. Pat. No. 4,310,519. The production, isolation, and structure determination of the avermectins are fully described in Albers-Schonberg et al., *J. Am. Chem. Soc.* 1981, 103, 4216–4221 and references cited therein. The conversion of natural avermectin $B_1$ to 22,23-dihydro-avermectin B1, the potent broad spectrum anthelminthic agent known as ivermectin, has also been described in the literature (Chabala et al., *J. Med. Chem.* 1980, 23, 1134–1136). The naturally occurring avermectins and the instant derivatives thereof have a very high degree of anthelminthic and anti-parasitic activity.

The naturally occurring avermectins are a series of macrocyclic lactones which are substituted at position 13 with a disaccharide consisting of two oleandrose residues. The preparation and properties of synthetic avermectin aglycones in which the disaccharide moiety has been removed leaving a free hydroxyl group at position 13 have been described by Mrozik et al., *J. Org. Chem.* 1982, 47, 489–492 and by Chabala et al., *J. Med. Chem.* 1980, 23, 1134–1136. The natural compounds have the following general structure:

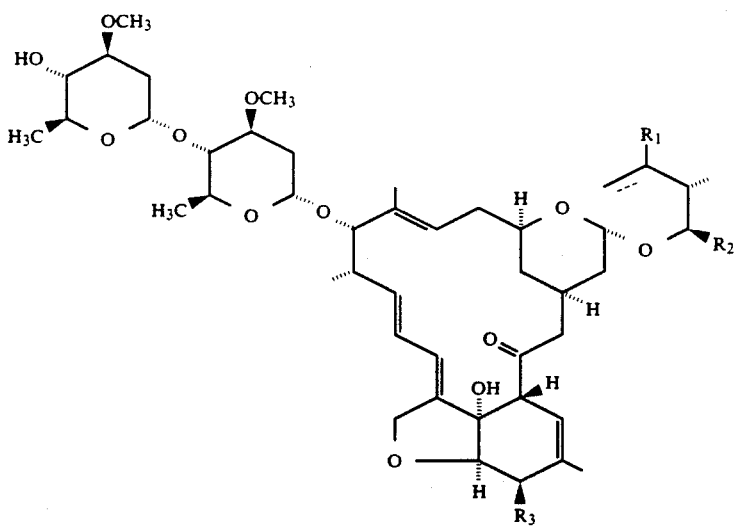

wherein the broken line at the 22,23-position indicates a single or double bond and;

$R_1$ is hydroxy and is present only when said broken line indicates a single bond;

$R_2$ is iso-propyl or sec-butyl; and $R_3$ is methoxy or hydroxy.

There are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | 22,23-bond | $R_1$ | $R_2$ | $R_3$ |
|---|---|---|---|---|
| A1a | double bond | — | sec-butyl | —$OCH_3$ |
| A1b | double bond | — | iso-propyl | —$OCH_3$ |
| A2a | single bond | —OH | sec-butyl | —$OCH_3$ |
| A2b | single bond | —OH | iso-propyl | —$OCH_3$ |
| B1a | double bond | — | sec-butyl | —OH |
| B1b | double bond | — | iso-propyl | —OH |
| B2a | single bond | —OH | sec-butyl | —OH |
| B2b | single bond | —OH | iso-propyl | —OH |

The avermectins are generally isolated as mixtures of the a and b components (typically $\geq 80\%$ a and $\leq 20\%$ b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components may be indicated by dropping the a or b from the designation of the compound. A mixture of avermectin B1a and avermectin B1b is thus referred to as avermectin B1. Alternatively a slash(/) is inserted between the compound designations to indicate a mixture such as in "B1a/B1b".

The above structural formula is shown without a definitive sterochemistry at certain portions and with a defined stereochemistry at other portions. However, during the course of the synthetic procedures used to prepare such compounds, or using racemization or epimerization procedures known to those skilled in the art, the products of such procedures can be a mixture of stereoisomers. In particular, the stereoisomers at the 13- and 23-positions may be oriented either α- or β-representing such groups being below or above the general plane of the molecule, respectively. In each such case, and at other positions in the molecule, both the α- and β- configurations are intended to be included within the ambit of this invention.

A related family of natural products is known as the milbemycins. The milbemycins have the same macrocyclic ring structure as the avermectins but have no substitution at position 13 and have a methyl or ethyl group at position 25 ($R_2$ = methyl or ethyl rather than isopropyl or sec-butyl as in the avermectins). The milbemycins and the fermentation conditions used to prepare them are described in U.S. Pat. No. 3,950,360. Closely related 13-deoxy-avermectin aglycones are prepared by chemical modification of the natural avermectins and have been described in U.S. Pat. Nos. 4,171,134 and 4,173,571.

Recently a number of related compounds have been described in European Patent Application EPO 170,006 and U.K. aplication 2,166,436 (see also Carter et al., *J. Antibiotics* 1988, 41, 519–529). These compounds are essentially 13-deoxy-avermectin aglycones in which the $R_2$ side chain contains a double bond and, in some cases, includes additional carbon atoms.

SUMMARY OF THE INVENTION

This invention is concerned with certain derivatives of avermectin aglycones in which a ketal funtionality has been introduced at position 13 and the use of these derivatives as antiparasitic agents. Thus it is an object of this invention to describe these avermectin derivatives. A further object of this invention is to describe processes for the preparation of these compounds. A still further object is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objects will become apparent from a reading of the following description.

DESCRIPTION OF THE INVENTION

The compounds of the instant invention are best realized in the following structure:

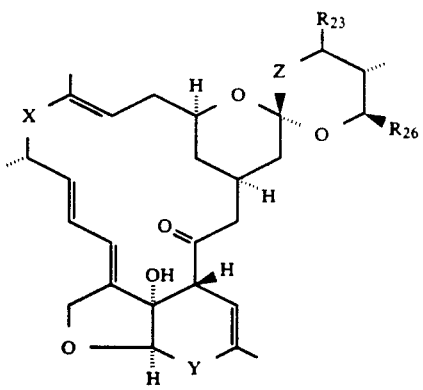

wherein:

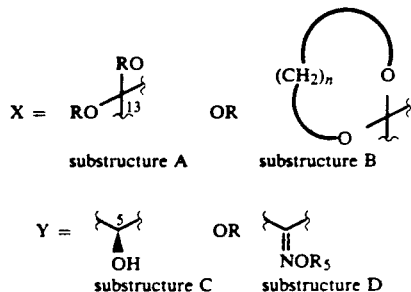

Z = single or double bond;

R = loweralkyl, phenyl, loweralkoxyloweralkyl, haloloweralkyl, loweralkenyl, loweralkynyl;
n = 2 or 3;
$R_5$ = H, loweralkyl;
$R_{23}$ = H, OH (OH only if Z = single bond); and
$R_{26}$ = loweralkyl, loweralkenyl.

In the instant invention "loweralkyl" is intended to include those alkyl groups of from 1 to 7 carbon atoms in either a straight or branched chain. Examples of such alkyl groups are methyl, ethyl, propyl, isopropyl, butyl, sec-butyl, pentyl, hexyl, heptyl, and the like.

The term "loweralkoxy" is intended to include those alkoxy groups of from 1 to 7 carbon atoms in either a straight or branched chain. Examples of such alkoxy groups are methoxy, ethoxy, propoxy, isopropoxy, butoxy, sec-butoxy, pentoxy, hexoxy, heptoxy, and the like.

The term "loweralkoxyloweralkyl" is intended to include those alkoxy substituted alkyl groups containing from 2 to 8 carbon atoms and from 1 to 3 oxygen atoms in either a straight or branched chain. Examples of such alkoxyalkyl groups include methoxymethyl, methoxyethoxymethyl, methoxyethoxyethoxymethyl, ethoxymethyl, ethoxymethyl, and the like.

The term "halogen" is intended to include the halogen atoms fluorine, chlorine, bromine, and iodine.

The term "haloloweralkyl" is intended to include those halogen substituted lower alkyl groups containing from 1 to 7 carbon atoms in either a straight or branched chain and from 1 to 3 halogen atoms. Examples of such haloalkyl groups include fluoromethyl, bromoethyl, chloropropyl, iodopentyl, and the like.

The term "loweralkenyl" is intended to include those alkenyl groups containing from 2 to 8 carbon atoms in either a straight or branched chain which contains 1 to 2 carbon-carbon double bonds. Examples of such alkenyl groups include allyl, butenyl, pentadienyl, hexenyl, and the like.

The term "loweralkynyl" is intended to include those alkynyl groups containing from 2 to 8 carbon atoms in either a straight or branched chain which contains 1 to 2 carbon-carbon triple bonds. Examples of such alkynyl groups include propargyl, butynyl, pentadiynyl, hexynyl, and the like.

Preferred compounds of this invention are realized when:

X = substructure A or substructure B;
Y = substructure C or substructure D;
Z = single or double bond;
R = loweralkyl, phenyl, loweralkoxyloweralkyl, haloloweralkyl, loweralkenyl, loweralkynyl;
n = 2 or 3;
$R_5$ = H, loweralkyl;
$R_{23}$ = H, OH (OH only if Z = single bond); and
$R_{26}$ = loweralkyl, loweralkenyl.

More preferred compounds of this invention are realized when:

X = substructure A or substructure B;
Y = substructure C or substructure D;
Z = single or double bond;
R = loweralkyl, loweralkoxyloweralkyl;
n = 2 or 3;
$R_5$ = H;
$R_{23}$ = H, OH (OH only if Z = single bond); and
$R_{26}$ = loweralkyl, loweralkenyl.

Still more preferred compounds of this invention are realized when:

X = substructure A or substructure B;

Y = substructure C;
Z = single or double bond;
R = loweralkyl;
n = 2 or 3;
$R_{23}$ = H, OH (OH only if Z = single bond); and
$R_{26}$ = loweralkyl, loweralkenyl.

The most preferred compounds of this invention are realized when:
X = substructure A or substructure B;
Z = single bond;
R = loweralkyl;
n = 2;
$R_{23}$ = H;
$R_{26}$ = loweralkyl.

Examples of the preferred compounds of this invention are as follows:

13-oxo-13-deoxy-22,23-dihydro-avermectin B1-aglycone-13-ethylene ketal;
13-oxo-13-deoxy-22,23-dihydro-avermectin B1-aglycone-13-methyl ketal;
13-oxo-13-deoxy-avermectin B1-aglycone-13-ethylene ketal;
13-oxo-13-deoxy-22,23-dihydro-avermectin B1-aglycone-13-ethylene ketal-5-oxime;
13-oxo-13-deoxy-avermectin B1-aglycone-13-ethylene ketal-5-methoxime;
13-oxo-13-deoxy-22,23-dihydro-avermectin B1-aglycone-13-phenyl ketal;
13-oxo-13-deoxy-22,23-dihydro-avermectin B1-aglycone-13-(2-methoxyethyl) ketal;
13-oxo-13-deoxy-22,23-dihydro-avermectin B1-aglycone-13-(2-fluoroethyl) ketal;
13-oxo-13-deoxy-22,23-dihydro-avermectin B1-aglycone-13-allyl ketal;
13-oxo-13-deoxy-22,23-dihydro-avermectin B1-aglycone-13-(3-butynyl) ketal;
13-oxo-13-deoxy-avermectin B1-aglycone-13-(1,3-dioxapropyl) ketal;
13-oxo-13-deoxy-26,27-didehydro-avermectin B2a-aglycone-13-ethylene ketal;
13-oxo-13-deoxy-22,23-dihydro-26,27-didehydro-avermectin B1a-aglycone-13-ethylene ketal.

PREPARATION OF STARTING MATERIALS

The starting materials for this invention are disclosed in Albers-Schonberg et al., *J. Am. Chem. Soc.* 1981, 103, 4216–4221 and references cited therein (naturally occurring avermectins), Chabala et al., *J. Med. Chem.* 1980, 23, 1134–1136 (22,23-dihydro-avermectin B1 (ivermectin), and 22,23-dihydro-avermectin B1-aglycone), Mrozik et al., *J. Org. Chem.* 1982, 47, 489–492 (avermectin aglycones), and U.K. application 2,166,436 (compounds with unsaturation in the $R_2$ side chain; see also Carter et al., *J. Antibiotics* 1988, 41, 519–529).

The novel compounds of this invention are prepared by the following procedures:

The hydroxyl group present at position 13 of the avermectin aglycones can be converted to a ketone by a number of oxidation procedures, including oxidation with dimethylsulfoxide (DMSO) based systems commonly known to those skilled in the art as Swern (or Moffatt) oxidations (DMSO-oxalyl chloride, DMSO-acetic anhydride, DMSO-trifluoracetic anhydride and the like) as well as oxidations with chromium based reagents (pyridinium chlorochromate, pyridinium dichromate, and the like) or other methods known to those skilled in the art. The DMSO based oxidation methods are preferred. These oxidations involve treating a solution of DMSO in a non-nucleophilic solvent such as dichloromethane, chloroform, ether, tetrahydrofuran and the like with an electrophilic activating agent such as oxalyl chloride (preferred), dicyclohexylcarbodiimide (DCC), phosgene, and the like at temperatures ranging from −90° C. to −55° C. and stirring the mixture thus formed at this temperature for 10 to 60 minutes. To the oxidizing reagent thus generated is added, at the same temperature, a solution of the alcohol in the solvent used to generate to reagent. The solution is stirred at temperatures ranging from −90° C. to −55° C. for 10 to 90 minutes then a hindered base such as triethylamine, diisopropylethylamine, and the like is added. The temperature is raised to 0° C. to 30° C. and the mixture stirred at this temperature for 10 to 90 minutes. The reaction is then worked up and the product isolated and purified using standard techniques known to those skilled in the art.

During the oxidation procedure it is necessary to protect other secondary hydroxyl groups in the molecule (note that it is not necessary to protect the tertiary hydroxyl present at position 7) with a protecting group which may be removed after the oxidation is accomplished. Suitable protecting groups include tert-butyldimethylsilyl, tert-butyldiphenylsilyl, phenoxyacetyl, acetyl, and the like. The tert-butyldimethylsilyl group is preferred and is introduced by treating a solution of the alcohol in dimethylformamide (DMF) with an excess of imidazole and a silylating reagent such as tert-butyldimethylsilyl-chloride, tert-butyldimethylsilyl-trifluoromethanesulfonate, and the like at temperatures ranging from 25° C. to 50° C. for 4 to 48 hours. The reaction is then worked up and the product isolated and purified using standard techniques known to those skilled in the art. The protecting group may be removed by treatment with a solution of p-toluenesulfonic acid (0.5-2%) in methanol at 0° C. to 25° C. for 0.5 to 8 hours. Alternatively, the protecting group may be removed by treatment with a solution of hydrogen fluoride in a pyridine/tetrahydrofuran solvent mixture. In both cases reaction workup and product isolation and purification are by standard techniques well known to those skilled in the art.

The ketal functionality is introduced at postion 13 by one of several methods. A solution of the ketone in the requisite alcohol (methanol for a methyl ketal, ethanol for an ethyl ketal, etc.) is treated with a strong acid such as p-toluenesulfonic acid, hydrochloric acid, phosphoric acid and the like or a lewis acid such as boron trifluoride etherate, aluminum chloride, and the like at temperatures ranging from 25° C. to the reflux temperature of the solvent for 1 to 64 hours. Alternatively, for high boiling alcohols the reaction may be performed in a non-hydrolxylic solvent such as tetrahydrofuran (THF), dioxane, ether, benzene and the like with one to ten molar equivalents of the alcohol added. In all of the above methods an agent is added to remove the water generated by ketal formation and thus drive the reaction to completion. Typical reagents for this purpose include the corresponding orthoformate or orthoacetate (trimethyl-orthoformate for methyl ketals, 1-methoxy-1,3-dioxolane for ethylene ketals, etc.) or the use of activated molecular sieves or azeotropic removal of water by performing the reaction in benzene. In all cases the reaction is worked up and the product isolated and purified using standard techniques known to those skilled in the art.

Oximes may be generated at position 5 via the 5-ketone. This ketone is prepared by oxidation of a compound with a 5-hydroxyl group using one of the oxidation methods described above. Oxidation with manganese dioxide is preferred. The oxidation is carried out by treating a solution of the alcohol in a non-hydroxylic solvent such as benzene, dichloromethane, chloroform, tetrahydrofuran, and the like with an excess of manganese dioxide at temperatures ranging from 25° C. to the reflux temperature of the solvent for 4 to 48 hours. The reaction is worked up and the product isolated and purified using standard techniques known to those skilled in the art. The ketone thus generated may be used to prepare oximes or alkoximes by a number of procedures. Generally, an excess of hydroxylamine hydrochloride or the appropriate alkoyxlamine hydrochloride (methoxylamine hydrochloride for a methoxime, etc.) is added to a solution of the ketone in pyridine and the solution stirred at temperatures ranging from 0° C. to 50° C. for 3-36 hours. Alternatively the amine hydrochloride is added to a solution of the ketone in a neutral solvent such as benzene, tetrahydrofuran, dioxane, dichloromethane, ethanol, and the like followed by a molar equivalent of a base such as sodium acetate, sodium hydroxide, triethylamine, and the like. The resulting mixture is stirred at temperatures ranging from 0° C. to 50° C. for 3-36 hours. In either case the reaction is worked up and the product isolated and purified using standard techniques known to those skilled in the art.

In the instances where the ultimate precursor is a milbemycin-type compound (lacks substitution at position 13) it is necessary to introduce a hydroxyl group at position 13. This may be accomplished by allylic oxidation of the C-14-15 olefin with selenium dioxide. The oxidation is effected by adding an excess of selenium dioxide to a solution of the olefin in a solvent such as ethanol, methanol formic acid, and the like. The mixture is stirred at temperatures ranging from 25° C. to reflux for 3-36 hours. The reaction is worked up and the product isolated and purified using standard techniques known to those skilled in the art. The resulting 13-hydroxy-analog is then oxidized to the 13-ketone using one of the oxidation procedures outlined above. Note that the stereochemistry of the hydroxyl group at position 13 is unimportant since this stereochemistry is lost in the conversion of the alcohol to the ketone.

The instant compounds of this invention are unexpectedly potent antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), *Musca domestica* (housefly) and against *Solenopsis Invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, and the like. Being amorphous the compounds are not characterized by sharp melting points but the chromatographic and analytical methods employed indicate that they are pure.

EXAMPLE 1

5-O-t-Butyldimethylsilyl-22,23-dihydro-avermectin B1 aglycone tert-Butyldimethylsilyl chloride (851 mg) was added to a solution of 22,23-dihydro-avermectin B1 aglycone (3.0 g, prepared as described in Chabala et al., *J. Med. Chem.* 1980, 23, 1134) and imidazole (873 mg) in 10 ml of dry dimethylformamide and the solution stirred at room temperature for 22 hours. The reaction mixture was partitioned between ether (50 ml) and water (100 ml). The aqueous layer was extracted with ether (2×20 ml) and the combined organic layers dried with magnesium sulfate, filtered and evaporated. The crude product was purified on a silica gel column eluted with 12.5% acetone in hexane to afford 1.97 g of a white foam which was identified by $^1$H NMR and mass spectrometry as 5-O-t-butyldimethylsilyl-22,23-dihydro-avermectin B1 aglycone.

EXAMPLE 2

5-O-t-Butyldimethylsilyl-13-oxo-13-deoxy-22,23-dihydro-avermectin B1-aglycone

Dimethyl sulfoxide (DMSO, 0.168 ml) was added to a cold (−78° C.) solution of oxalyl chloride (0.100 ml) in 5 ml of dry dichloromethane and the solution stirred at −78° C. for 20 minutes. A solution of 5-O-t-butyldimethylsilyl-22,23-dihydro-avermectin B1 aglycone (500 mg) in 10 ml of dry dichloromethane was then added and the solution stirred at −78° C. for 45 minutes. Triethylamine (0.720 ml) was then added and the mixture warmed to room temperature and stirred at room temperature for 45 minutes. The mixture was partitioned between water (75 ml) and dichloromethane (35 ml). The aqueous layer was extracted with dichloromethane (2×35 ml) and the combined organic layers dried with magnesium sulfate, filtered and evaporated. The crude product was purified on a silica gel column eluted with 9% acetone in hexane to afford 380 mg of a light yellow oil which was identified by $^1$H NMR and mass spectrometry as 5-O-t-butyldimethylsilyl113-oxo-13-deoxy-22,23-dihydro-avermectin B1-aglycone.

EXAMPLE 3

13-Oxo-13-deoxy-22,23-dihydro-avermectin B1-aglycone

Water (10 ml) and p-toluenesulfonic acid (1.6 g) were added to a cold (0° C.) solution of 5-O-t-butyldimethylsilyl-13-oxo-13-deoxy-22,23-dihydro-avermectin B1-aglycone (2.85 g) in 160 ml of methanol. The solution was allowed to stand in a refrigerator (ca. 5° C.) for 7 hours then partitioned between dichloromethane (75 ml) and 5% aqueous sodium bicarbonate (75 ml). The aqueous layer was extracted with dichloromethane (3×75 ml) and the combined organic layers dried with magnesium sulfate, filtered and evaporated. The crude product was purified on a silica gel column eluted with 25% acetone in hexane to afford 1.65 g of a light yellow foam which was identified by $^1$H NMR and mass spectrometry as 13-oxo-13-deoxy-22,23-dihydro-avermectin B1-aglycone.

EXAMPLE 4

13-Oxo-13-deoxy-22,23-dihydro-avermectin B1-aglycone-13-ethylene ketal

Ethylene glycol (0.110 ml) and 2-methoxy-1,3-dioxolane (0.190 ml, Aldrich Chemical Co.) were added to a solution of 13-oxo-13-deoxy-22,23-dihydro-avermectin B1-aglycone (115 mg) in 5 ml of dry toluene. Boron trifluoride etherate (0.025 ml) was then added and the solution stirred at room temperature for 63 hours. The mixture was partitioned between ether (3 ml) and 5% aqueous sodium bicarbonate. The aqueous layer was extracted with ether (3×5 ml) and the combined organic layers dried with magnesium sulfate, filtered and evaporated. The crude product was purified by preparative layer chromatography on a 1.5 mm silica gel plate eluted with 50% ethyl acetate in hexane to afford 87 mg of a light yellow oil. This oil was further purified by preparative layer chromatography on a 1.0 mm silica gel plate eluted with 15% ethyl acetate in dichloromethane to afford 80 mg of a colorless oil which was identified by $^1$H NMR and mass spectrometry as 13-oxo-13-deoxy-22,23-dihydro-avermectin B1-aglycone-13-ethylene-ketal.

EXAMPLE 5

13-Oxo-13-deoxy-22,23-dihydro-avermectin B1-aglycone-13-methyl ketal

Trimethyl orthoformate (0.050 ml) was added to a solution of 13-oxo-13-deoxy-22,23-dihydro-avermectin B1-aglycone (25 mg) in 1.5 ml of dry methanol. Boron trifluoride etherate (0.005 ml) was then added and the solution stirred at room temperature for 80 minutes. The mixture was partitioned between ether (5 ml) and 5% aqueous sodium bicarbonate (2 ml). The aqueous layer was extracted with ether (3×5 ml) and the combined organic layers dried with magnesium sulfate, filtered and evaporated. The crude product was purified by preparative layer chromatography on a 0.5 mm silica gel plate eluted with 25% acetone in hexane to afford 10 mg of a light yellow oil. This oil was further purified by preparative layer chromatography on a 0.25 mm silica gel plate eluted with 50% ethyl acetate in hexane to afford a colorless oil which was identified by $^1$H NMR and mass spectrometry as 13-oxo-13-deoxy-22,23-dihydro-avermectin B1-aglycone-13-methyl ketal.

EXAMPLE 6

5-O-t-Butyldimethylsilyl-avermectin B1-aglycone tert-Butyldimethylsilyl chloride (35 mg) was added to a solution of avermectin B1 aglycone (124 mg, prepared as described in Mrozik et al., *J. Org. Chem.* 1982, 47, 489) and imidazole (36 mg) in 2.5 ml of dry dimethylformamide and the solution stirred at room temperature for 24 hours. The reaction mixture was partitioned between ether (25 ml) and water (25 ml). The aqueous layer was extracted with ether (20 ml) and the combined organic layers dried with magnesium sulfate, filtered and evaporated. The crude product was purified by preparative layer chromatography on a 2.0 mm silica gel plate eluted with 25% acetone in hexane to afford 82 mg of a white foam which was identified by $^1$H NMR and mass spectrometry as 5-O-t-butyldimethylsilyl-avermectin B1 aglycone.

EXAMPLE 7

5-O-t-Butyldimethylsilyl-13-oxo-13-deoxy-avermectin B1-aglycone

Dimethyl sulfoxide (DMSO, 0.028 ml) was added to a cold (−78° C.) solution of oxalyl chloride (0.016 ml) in 2 ml of dry dichloromethane and the solution stirred at −78° C. for 20 minutes. A solution of 5-O-t-butyldimethylsilyl-avermectin B1 aglycone (82 mg) in 2 ml of dry dichloromethane was then added and the solution stirred at −78° C. for 45 minutes. Triethylamine (0.118 ml) was then added and the mixture warmed to room temperature and stirred at room temperature for 45 minutes. The mixture was partitioned between water (5 ml) and dichloromethane (5 ml). The aqueous layer was extracted with dichloromethane (2×35 ml) and the combined organic layers dried with magnesium sulfate, filtered and evaporated. The crude product was purified by preparative layer chromatography on a 1.0 mm silica gel plate eluted with 9% acetone in hexane to afford 64 mg of a colorless oil which was identified by $^1$H NMR and mass spectrometry as 5-O-t-butyldimethylsilyl-13-oxo-13-deoxy-avermectin B1-aglycone.

EXAMPLE 8

13-Oxo-13-deoxy-avermectin B1-aglycone

Water (0.2 ml) and p-toluenesulfonic acid (35 mg) were added to a cold (0° C.) solution of 5-O-t-butyldimethylsilyl-13-oxo-13-deoxy-avermectin B1-aglycone (64 mg) in 3.5 ml of methanol. The solution was allowed to stand in a refrigerator (ca. 5° C.) for 23 hours then partitioned between dichloromethane (3 ml) and 5% aqueous sodium bicarbonate (3 ml). The aqueous layer was extracted with dichloromethane (3×5 ml) and the combined organic layers dried with magnesium sulfate, filtered and evaporated. The crude product was purified by preparative layer chromatography on a 1.0 mm silica gel plate eluted with 25% acetone in hexane to afford 35 mg of a colorless oil which was identified by $^1$H NMR and mass spectrometry as 13-oxo-13-deoxy-avermectin B1-aglycone.

EXAMPLE 9

13-Oxo-13-deoxy-avermectin B1-aglycone-13-ethylene ketal

Ethylene glycol (0.035 ml) and 2-methoxy-1,3-dioxolane (0.060 ml) were added to a solution of 13-oxo-13-deoxy-avermectin B1-aglycone (35 mg) in 1.5 ml of dry toluene. Boron trifluoride etherate (0.008 ml) was then added and the solution stirred at room temperature for 21.5 hours. The mixture was partitioned between ether (5 ml) and 5% aqueous sodium bicarbonate. The aqueous layer was extracted with ether (3×5 ml) and the combined organic layers dried with magnesium sulfate, filtered and evaporated. The crude product was purified by preparative layer chromatography on a 0.5 mm silica gel plate eluted with 25% acetone in hexane to afford 24 mg of a colorless oil which was identified by $^1$H NMR and mass spectrometry as 13-oxo-13-deoxy-avermectin B1-aglycone-13-ethylene-ketal.

EXAMPLE 10

13-Oxo-13-deoxy-22,23-dihydro-avermectin B1-aglycone-13-(1,3-dioxapropyl) ketal 1,3-Propanediol (0.250 ml) and activated 3A molecualr sieves are added to a solution of 13-oxo-13-deoxy-22,23-dihydro-avermectin B1-aglycone (100 mg) in 5 ml of dry toluene. Boron trifluoride etherate (0.025 ml) is then added and the solution stirred at room temperature until complete by analytical TLC. The mixture is partitioned between ether (3 ml) and 5% aqueous sodium bicarbonate and the aqueous layer extracted with ether (3×5 ml). The combined organic layers are dried with magnesium sulfate, filtered and evaporated. The crude product is purified by preparative layer chromatography on a silica gel plate to afford 13-oxo-13-deoxy-22,23-dihydro-avermectin B1-aglycone-13-(1,3-dioxapropyl) ketal which is identified by $^1$H NMR and mass spectrometry.

EXAMPLE 11

13-Oxo-13-deoxy-22,23-dihydro-avermectin B1-aglycone-13-(2-methoxyethyl) ketal

Substitution of 2-methoxyethanol for 1,3-propanediol in the procedure of example 10 affords 13-oxo-13-deoxy-22,23-dihydro-avermectin B1-aglycone-13-(2-methoxyethyl)-ketal which is identified by $^1$H NMR and mass spectrometry.

EXAMPLE 12

13-Oxo-13-deoxy-22,23-dihydro-avermectin B1-aglycone-13-(2-fluoroethyl) ketal

Substitution of 2-fluoroethanol for 1,3-propanediol in the procedure of Example 10 affords 13-oxo-13-deoxy-22,23-dihydro-avermectin B1-aglycone-13-(2-fluoroethyl)-ketal which is identified by $^1$H NMR and mass spectrometry.

EXAMPLE 13

13-Oxo-13-deoxy-22,23-dihydro-avermectin B1-aglycone-13-allyl ketal

Substitution of allyl alcohol for 1,3-propanediol in the procedure of Example 10 affords 13-oxo-13-deoxy-22,23-dihydro-avermectin B1-aglycone-13-allyl-ketal which is identified by $^1$H NMR and mass spectrometry.

EXAMPLE 14

13-Oxo-13-deoxy-22,23-dihydro-avermectin B1-aglycone-13-phenyl ketal

Substitution of phenol for 1,3-propanediol in the procedure of Example 10 affords 13-oxo-13-deoxy-22,23-dihydro-avermectin B1-aglycone-13-phenyl-ketal which is identified by $^1$H NMR and mass spectrometry.

EXAMPLE 15

13-Oxo-13-deoxy-22,23-dihydro-avermectin B1-aglycone-13-(3-butynl) ketal

Substitution of 3-butyn-1-ol for 1,3-propanediol in the procedure of Example 10 affords 13-oxo-13-deoxy-22,23-dihydro-avermectin B1-aglycone-13-(3-butynl)-ketal which is identified by $^1$H NMR and mass spectrometry.

EXAMPLE 16

5-Oxo-13-oxo-13-deoxy-22,23-dihydro-avermectin B1-aglycone-13-ethylene ketal

Manganese dioxide (42 mg) is added to a solution of 100 mg of 13-oxo-13-deoxy-22,23-dihydro-avermectin B1-aglycone-13-ethylene ketal in 5 ml of dry benzene. The resulting mixture is stirred at 35° C. until complete by analytical thin layer chromatography. The mixture is partitioned between ether (5 ml) and water (5 ml) and the aqueous layer extracted with ether (3×5 ml). The combined organic layers are dried with magnesium sulfate, filtered and evaporated. The crude product is purified by preparative layer chromatography on a silica gel plate to afford 5-oxo-13-oxo-13-deoxy-22,23-dihydro-avermectin B1-aglycone-13-ethylene ketal which is identified by $^1$H NMR and mass spectrometry.

EXAMPLE 17

13-Oxo-13-deoxy-22,23-dihydro-avermectin B1-aglycone-5-oxime-13-ethylene ketal

Hydroxylamine hydrochloride (44 mg) is added to a solution of 5-oxo-13-oxo-13-deoxy-22,23-dihydro-avermectin B1-aglycone-13-ethylene ketal (100 mg) in 3 ml of dry pyridine. The solution is stirred at room temperature until complete by analytical thin layer chromatography then partitioned between ether (10 ml) and water (10 ml) and the aqueous layer extracted with ether (2×5 ml). The combined organic layers are dried with magnesium sulfate, filtered and evaporated. The crude product is purified by preparative layer chromatography on a silica gel plate to afford 13-oxo-13-deoxy-22,23-dihydro-avermectin B1-aglycone-13-ethylene ketal-5-oxime which is identified by $^1$H NMR and mass spectrometry.

EXAMPLE 18

13-Oxo-13-deoxy-22,23-dihydro-avermectin B1-aglycone-5-methoxime-13-ethylene ketal Methoxylamine hydrochloride (60 mg) is added to a solution of 5-oxo-13-oxo-13-deoxy-22,23-dihydro-avermectin B1-aglycone-13-ethylene ketal (100 mg) in 3 ml of dry pyridine. The solution is stirred at room temperature until complete by analytical thin layer chromatography then partitioned between ether (10 ml) and water (10 ml) and the aqueous layer extracted with ether (2×5 ml). The combined organic layers are dried with magnesium sulfate, filtered and evaporated. The crude product is purified by preparative layer chromatography on a silica gel plate to afford 13-oxo-13-deoxy-22,23-dihydro-avermectin B1-aglycone-13-ethylene ketal-5-methoxime which is identified by $^1$H NMR and mass spectrometry.

EXAMPLE 19

26,27-Didehydro-avermectin B2a aglycone

Selenium dioxide (78 mg) is added to a solution of 26,27-didehydro-13-deoxy-avermectin B2a aglycone (100 mg, see Carter et al., *J. Antibiotics* 1988, 41, 519–529.) in 4 ml of ethanol and the resulting solution is refluxed for 8 hours. The mixture is partitioned between ether (10 ml) and 5% aqueous sodium bicarbonate (5 ml) and the aqueous layer extracted with ether (3×5 ml). The combined organic layers are dried with magnesium sulfate, filtered and evaporated. The crude product, which consists of a mixture of alcohols, is purified by preparative layer chromatography on a silica gel plate. The band corresponding to the desired product is isolated to afford 26,27-didehydro-avermectin B2a aglycone which is identified by $^1$H NMR and mass spectrometry.

EXAMPLE 20

5,23-Bis-O-tert-butyldimethylsilyl-26,27-didehydro-avermectin B2a aglycone tert-Butyldimethylsilyl chloride (70 mg) is added to a solution of 26,27-didehydro-avermectin B2a aglycone (120 mg) and imidazole (75 mg) in 2.5 ml of dry dimethylformamide and the solution stirred at 35° C. for 24 hours. The reaction mixture is partitioned between ether (25 ml) and water (25 ml). The aqueous layer is extracted with ether (20 ml) and the combined organic layers dried with magnesium sulfate, filtered and evaporated. The crude product, which consists of a mixture of isomers, is purified by preparative layer chromatography on a silica gel plate. The band corresponding to the desired product is isolated and identified by $^1$H NMR and mass spectrometry as 5,23-bis-O-t-butyldimethylsilyl-26,27-didehydro-avermectin B2a aglycone.

EXAMPLE 21

13-Oxo-13-deoxy-5,23-bis-O-tert-butyldimethylsilyl-26,27-didehydro-avermectin B2a aglycone Oxidation of 5,23-bis-O-t-butyldimethylsilyl-26,27-didehydro-avermectin B2a aglycone according to the procedure of Example 2 affords 13-oxo-13-deoxy-5,23-bis-O-t-butyldimethylsilyl-26,27-didehydro-avermectin B2a aglycone which is identified by $^1$H NMR and mass spectrometry.

EXAMPLE 22

13-Oxo-13-deoxy-26,27-didehydro-avermectin B2a aglycone

Treatment of 13-oxo-13-deoxy-5,23-bis-O-t-butyldimethylsilyl-26,27-didehydro-avermectin B2a aglycone with p-toluenesulfonic acid according to the procedure of Example 3 affords 13-oxo-13-deoxy-26,27-didehydro-avermectin B2a aglycone which is identified by $^1$H NMR and mass spectrometry.

EXAMPLE 23

13-Oxo-13-deoxy-26,27-didehydro-avermectin B2a aglycone-13-ethylene ketal

Reaction of 13-oxo-13-deoxy-26,27-didehydro-avermectin B2a aglycone with ethylene glycol as described in Example 4 affords 13-oxo-13-deoxy-26,27-didehydro-avermectin B2a aglycone-13-ethylene ketal which is identified by $^1$H NMR and mass spectrometry.

EXAMPLE 24

26,27-Didehydro-22,23-dihydro-avermectin B1a aglycone

Oxidation of 26,27-didehydro-22,23-dihydro-13-deoxy-avermectin B1a aglycone (see EP application 262384) with selenium dioxide as described in Example 19 affords (after purification) 26,27-didehydro-22,23-dihydro-avermectin B1a aglycone which is identified by $^1$H NMR and mass spectrometry.

EXAMPLE 25

5-O-t-Butyldimethylsilyl-26,27-didehydro-22,23-dihydro-avermectin B1a aglycone Silylation of 26,27-didehydro-22,23-dihydro-avermectin B1a agloycone as described in Example 1 affords 5-O-t-butyldimethylsily-26,27-didehydro-22,23-dihydro-avermectin B1a aglycone which is identified by $^1$H NMR and mass spectrometry.

EXAMPLE 26

5-O-t-Butyldimethylsilyl-13-oxo-13-deoxy-26,27-didehydro-22,23-dihydro-avermectin B1a aglycone Oxidation of 5-O-t-butyldimethylsily-26,27-didehydro-22,23-dihydro-avermectin B1a aglycone according to the procedure of Example 2 affords 13-oxo-13-deoxy-5-O-t-butyldimethylsilyl-26,27-didehydro-22,23-dihydro-avermectin B1a aglycone which is identified by $^1$H NMR and mass spectrometry.

EXAMPLE 27

13-Oxo-13-deoxy-26,27-didehydro-22,23-dihydro-avermectin B1a aglycone

Treatment of 13-oxo-13-deoxy-5-O-t-butyldimethylsily-26,27-didehydro-22,23-dihydro-avermectin B1a aglycone with p-toluenesulfonic acid according to the procedure of Example 3 affords 13-oxo-13-deoxy-26,27-didehydro-22,23-dihydro-avermectin B1a aglycone which is identified by $^1$H NMR and mass spectrometry.

EXAMPLE 28

13-Oxo-13-deoxy-26,27-didehydro-22,23-dihydro-avermectin B1a aglycone-13-ethylene ketal Reaction of 13-oxo-13-deoxy-26,27-didehydro-22,23-dihydro-avermectin B1a aglycone with ethylene glycol as described in Example 4 affords 13-oxo-13-deoxy- 26,27-didehydro-22,23-dihydro-avermectin B1a aglycone-13-ethylene ketal which is identified by $^1$H NMR and mass spectrometry.

What is claimed is:

1. A compound having the formula:

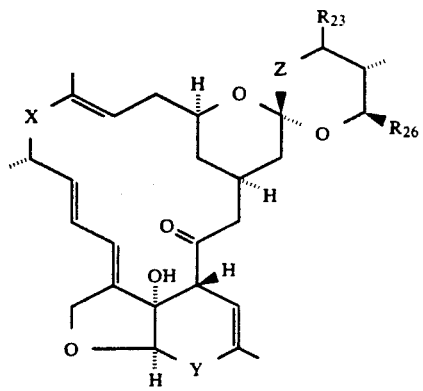

wherein:

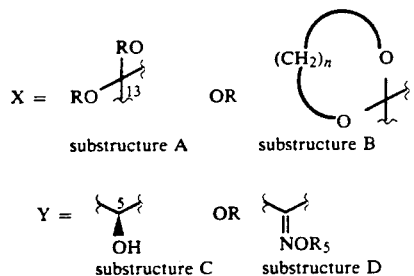

Z = single or double bond;
R = loweralkyl, phenyl, loweralkoxyloweralkyl, haloloweralkyl, loweralkenyl, loweralkynyl;
n = 2 or 3;
$R_5$ = H, loweralkyl;
$R_{23}$ = H, OH (OH only if Z = single bond); and
$R_{26}$ = loweralkyl, loweralkenyl.

2. The compound of claim 1 wherein:
X = substructure A or substructure B;
Y = substructure C or substructure D;
Z = single or double bond;
R = loweralkyl, loweralkoxyloweralkyl;
n = 2 or 3;
$R_5$ = H;
$R_{23}$ = H, OH (OH only if Z = single bond); and
$R_{26}$ = loweralkyl, loweralkenyl.

3. The compound of claim 2 wherein:
X = substructure A or substructure B;
Y = substructure C;
Z = single or double bond;
R = loweralkyl;
n = 2 or 3;
$R_{23}$ = H, OH (OH only is Z = single bond); and
$R_{26}$ = loweralkyl, loweralkenyl.

4. The compound of claim 3 wherein:
X = substructure A or substructure B;
Z = single bond;
R = loweralkyl;
n = 2;
$R_{23}$ = H, OH (OH only if Z = single bond); and
$R_{26}$ = methyl, ethyl, isopropyl, or sec-butyl.

5. The compound of claim 4 wherein:
X = substructure A or substructure B;
R = methyl;
n = 2;
$R_{23}$ = H; and
$R_{26}$ = isopropyl or sec-butyl.

6. The compound of claim 1 which is 13-oxo-13-deoxy-22,23-dihydro-avermectin B1-aglycone-13-ethylene ketal.

7. The compound of claim 1 which is 13-oxo-13-deoxy-22,23-dihydro-avermectin B1-aglycone-13-methyl ketal.

8. The compound of claim 1 which is 13-oxo-13-deoxy-avermectin B1-aglycone-13-ethylene ketal.

9. The compound of claim 1 which is 13-oxo-13-deoxy-22,23-dihydro-avermectin B1-aglycone-13-ethylene ketal-5-oxime.

10. The compound of claim 1 which is 13-oxo-13-deoxy-avermectin B1-aglycone-13-ethylene ketal-5-methoxime.

11. The compound of claim 1 which is 13-oxo-13-deoxy-avermectin B1-aglycone-13-(1.3-dioxapropyl) ketal.

12. The compound of claim 1 which is 13-oxo-13-deoxy-26,27-didehydro-avermectin B2a-aglycone-13-ethylene ketal.

13. The compound of claim 1 which is 13-oxo-13-deoxy-22,23-dihydro-26,27-didehydro-avermectin B1a-aglycone-13-ethylene ketal.

14. A method for the treatment or prevention of parasitic infections in animals which comprises treating such animals with an effective amount of a compound of claim 1.

15. A method for the treatment of pests of plants which comprises treating said plants or the soil in which they grow with an effective amount of a compound of claim 1.

16. A composition useful for the treatment or prevention of parasitic infections of animals or for the treatment of pests of plants which is comprised of an inert carrier and a compound of claim 1.

* * * * *